(12) United States Patent
Juutilainen

(10) Patent No.: US 10,828,598 B2
(45) Date of Patent: Nov. 10, 2020

(54) ARRANGEMENT AND PROCESS FOR RECOVERY OF CARBON DIOXIDE FROM GAS USING AN ABSORPTION TANK HOUSING AND AGITATOR

(71) Applicant: CARBONREUSE FINLAND OY, Savonlinna (FI)

(72) Inventor: Timo Juutilainen, Savonlinna (FI)

(73) Assignee: CARBONREUSE FINLAND OY, Savonlinna (FI)

( * ) Notice: Subject to any disclaimer, the term of this patent is extended or adjusted under 35 U.S.C. 154(b) by 844 days.

(21) Appl. No.: 15/482,199

(22) Filed: Apr. 7, 2017

(65) Prior Publication Data

US 2017/0209826 A1    Jul. 27, 2017

Related U.S. Application Data

(63) Continuation of application No. PCT/FI2015/050674, filed on Oct. 8, 2015.

(30) Foreign Application Priority Data

Oct. 9, 2014    (FI) .................................. 20145887

(51) Int. Cl.
*B01D 3/14*    (2006.01)
*B01D 53/14*    (2006.01)
(Continued)

(52) U.S. Cl.
CPC ........... *B01D 53/1475* (2013.01); *B01D 3/14* (2013.01); *B01D 53/1425* (2013.01);
(Continued)

(58) Field of Classification Search
CPC ...... B01D 2252/103; B01D 2252/2021; B01D 2258/0283; B01D 3/14; B01D 53/1425;
(Continued)

(56) References Cited

U.S. PATENT DOCUMENTS

2009/0014376 A1*  1/2009  Huhta-Koivisto .... C02F 1/5236
                                                              210/242.2
2009/0307975 A1   12/2009  Wolf
                  (Continued)

FOREIGN PATENT DOCUMENTS

EP    1 277 706 A2    1/2003
EP    2 292 322 A2    3/2011
              (Continued)

OTHER PUBLICATIONS

Communication pursuant to Article 94(3) EPC issued by the European Patent Office in relation to European Application No. 15 798 487.3 dated Mar. 20, 2019 (7 pages).
(Continued)

*Primary Examiner* — Cabrena Holecek
(74) *Attorney, Agent, or Firm* — Robert P. Michal, Esq.; Carter, DeLuca & Farrell LLP

(57) ABSTRACT

A system and a method for the recovery of carbon dioxide from a gas containing it. The system of the invention includes:
 pressurizing means for pressurizing the gas, an absorption tank for absorbing into water the carbon dioxide contained in a gas pressurized with the pressurizing means, a desorption tank for desorbing from water the carbon dioxide absorbed in water, means for circulating water from the absorption tank into the desorption tank and from the desorption tank back into the absorption tank, and recovering means for the recovery of carbon dioxide capable of being desorbed from the water. The system's absorption tank houses an agitator with a function of enabling water to circulate in the absorption tank by ejecting it into an air space of the absorption tank and by spreading in the absorption tank's air space over an area as extensive as possible.

7 Claims, 4 Drawing Sheets

(51) Int. Cl.
*B01D 53/18* (2006.01)
*C07C 29/151* (2006.01)
*C25B 1/10* (2006.01)
*C25B 9/10* (2006.01)
*C25B 9/08* (2006.01)
*C25B 15/08* (2006.01)
*C25B 3/04* (2006.01)
*C01B 32/50* (2017.01)

(52) U.S. Cl.
CPC ........... *B01D 53/18* (2013.01); *B01D 53/185* (2013.01); *C01B 32/50* (2017.08); *C07C 29/1518* (2013.01); *C25B 1/10* (2013.01); *C25B 3/04* (2013.01); *C25B 9/08* (2013.01); *C25B 9/10* (2013.01); *C25B 15/08* (2013.01); *B01D 2252/103* (2013.01); *B01D 2252/2021* (2013.01); *B01D 2258/0283* (2013.01); *Y02C 20/40* (2020.08); *Y02E 60/36* (2013.01); *Y02P 20/129* (2015.11); *Y02P 20/151* (2015.11)

(58) Field of Classification Search
CPC .. B01D 53/1475; B01D 53/18; B01D 53/185; C01B 32/50; C07C 29/1518; C25B 15/08; C25B 1/10; C25B 3/04; C25B 9/08; C25B 9/10; Y02C 10/06; Y02E 60/366; Y02P 20/129; Y02P 20/152
See application file for complete search history.

(56) References Cited

U.S. PATENT DOCUMENTS

| | | |
|---|---|---|
| 2011/0229393 A1 | 9/2011 | Hu |
| 2012/0132074 A1 | 5/2012 | Koslow et al. |
| 2012/0226080 A1 | 9/2012 | Meyer-Pittroff |
| 2015/0174530 A1* | 6/2015 | Murai ................ B01D 53/62 423/210 |

FOREIGN PATENT DOCUMENTS

| | | |
|---|---|---|
| FI | 20045086 A | 9/2005 |
| FI | 124060 B | 2/2014 |
| JP | H 11188386 A | 7/1999 |
| JP | 3637195 B2 | 4/2005 |
| WO | WO-2013 079116 A1 | 6/2013 |

OTHER PUBLICATIONS

Finnish Search Report issued by the Finnish Patent Office in relation to Finnish Application No. 20145887 dated Jun. 3, 2015 (2 pages).
Finnish Official Action issued by the Finnish Patent Office in relation to Finnish Application No. 20145887 dated Feb. 3, 2017 (4 pages).
Written Opinion of the International Searching Authority issued by the European Patent Office in relation to International Patent Application No. PCT/FI2015/050674 dated Feb. 17, 2016 (7 pages).
International Search Report issued by the European Patent Office issued in relation to International Patent Application No. PCT/FI2015/050674 dated Feb. 17, 2016. (4 pages).

* cited by examiner

ARRANGEMENT AND PROCESS FOR RECOVERY OF CARBON DIOXIDE FROM GAS USING AN ABSORPTION TANK HOUSING AND AGITATOR

CROSS-REFERENCED TO RELATED APPLICATIONS

This application is a continuation of PCT Patent Application No. PCT/FI2015/050674 filed Oct. 8, 2015, which claims the benefit under 35 USC §119(e) to Finnish Patent Application No. 20145887, filed Oct. 9, 2014, the disclosure of each of these applications are expressly incorporated herein by reference in their entireties.

BACKGROUND INFORMATION

One object of the invention is a system for the recovery of carbon dioxide from a gas which contains it, said system including:
  pressurizing means for pressurizing the gas
  an absorption tank for absorbing into water the carbon dioxide contained in a gas pressurized with the pressurizing means
  a desorption tank for desorbing from water the carbon dioxide absorbed in water
  means for circulating water from the absorption tank into the desorption tank and from the desorption tank back into the absorption tank
  recovering means for the recovery of carbon dioxide to be desorbed from the water.

Another object of the invention is a method for the recovery of carbon dioxide from a gas which contains it, said method including:
  pressurizing the gas
  absorbing carbon dioxide contained in the pressurized gas into water in an absorption tank
  desorbing carbon dioxide absorbed in water from water in a desorption tank
  circulating water from the absorption tank into the desorption tank and from the desorption tank back into the absorption tank
  recovering carbon dioxide desorbed from the water.

In connection with this invention, the "carbon dioxide -containing gas" or the like expressions refer to a gas mixture which contains not only carbon dioxide gas but also at least one other substance in gaseous form.

The recovery of carbon dioxide has traditionally involved the use of a so-called fill block column. It comprises a sizable tank filled with loose blocks. From a top end of the tank is poured water so as to soak the loose blocks, and from a bottom end is supplied a flue gas or the like carbon dioxide -containing gas. The surface of the loose blocks constitutes a large area, thereby enhancing the absorption taking place at an interface between gas and water. Gas and water are supplied from the opposite ends for the purpose of generating a so-called countercurrent process, in which the absorption gradient remains high across the entire column. In boilers, the same countercurrent principle is referred to as superheating. A drawback with the fill block column is a remarkably large size and thereby also the purchase price.

In recent times, so-called amine processes have penetrated the market. These do not use pure water, which is generally the case with fill block columns, but water has amines admixed therein. As a result, the absorption capability of water improves to multiple tenfold, but there is a drawback of higher costs with a necessity to regenerate such chemicals. A second drawback is that a part of the chemicals end up annually in the environment. According to one estimate, as much as 1% of the employed amines end up annually in the environment. There exists also such a version of amine processes which additionally makes use of enzymes to enhance the process and to reduce the use of amines.

A third prior known method is the bubble column, wherein a tank is full of water and flue gas is supplied as small bubbles from the bottom of the tank. This results in a large surface area since the bubbles are as small as possible. A drawback again is quite a large size of the column.

The general principle of a recovery process is that the process comprises an absorption column in which carbon dioxide is absorbed into water and other gases pass through the column and are conducted into a smokestack. Such selectivity is a result of different gases having a different absorption capability into water, according to Henry's law. The flue gas contains mainly nitrogen, as does also the air used in combustion, but oxygen present in the air converts into carbon dioxide in the combustion process. Carbon dioxide is absorbed into water by approximately hundred-fold with respect to nitrogen and the absorption rate of possible oxygen lies between those two.

The water saturated with carbon dioxide is conducted from the absorption column to the desorption column with an effort to provide in the latter such conditions that carbon dioxide reconverts back into gas. As known, absorption and desorption are influenced by temperature and pressure, as well as by the partial pressures of gases. By establishing a reasonably high pressure in the absorption column or tank and/or by using cold water, the result will be a good absorption, and in a reverse case, i.e. a low pressure and/or a higher temperature in the desorption column or tank, the gas is enabled in desorption to remove itself from water and to become a gas again. Both the pressurization and the change of temperature require energy and, hence, must be used prudentially. A third prior known method of enhancing the process is agitation. In a preferred case, the interface between gas and water can be made large as well as constantly changing with abundant agitation. A drawback of this, with currently employed agitators, is the considerable consumption of energy.

The boundary activities occurring at an interface between water and gas, such as absorption and desorption, suffer from such a problem that, in the close proximity of water, what has become absorbed from gas into water are those gases therein which are capable of being absorbed. In other words, the interfacial gas is microscopically "void" of carbon dioxide. On the other hand, at a boundary surface of water, in the intimate vicinity of gas, the water has already become saturated with the discussed absorbable gas and hence, does not agree to take up any more carbon dioxide. The process stalls unless some sort of agitation takes place. The problem is referred to as a "two-layer problem". In the fill block column, the movement of flowing water agitates the water a little bit, so some fresh under-saturated water arrives again at the interface and the gas travels between the fill blocks, thereby agitating the surface of the gas. A similar type of phenomenon takes place also in the bubble column. The agitation taking place in both cases is nevertheless very modest.

SUMMARY

In this invention, the prior art problems are resolved by generating an energy efficient, yet such a powerful agitation that the two-layer problem does not arise and the reactions are accelerated at the same time.

The system according to the invention is characterized in that the absorption tank houses an agitator with a function of enabling water to circulate in the absorption tank by ejecting it into an air space of the absorption tank and by spreading it in the absorption tank's air space over an area as extensive as possible. What is achieved this way is that the carbon dioxide contained in a gas, such as e.g. in a flue gas, will be absorbed as effectively as possible into the mass of water contained in the absorption tank.

In one particularly preferred embodiment of the system of the invention, the desorption tank also houses an agitator with a function of enabling water to circulate in the desorption tank by ejecting it into an air space of the desorption tank and by spreading it in the desorption tank's air space over an area as extensive as possible. What is achieved this way is that the carbon dioxide of water that has been conducted from the absorption tank into the desorption tank and that has absorbed carbon dioxide therein will be desorbed as effectively as possible in the desorption tank.

It is preferable in the system of the invention and in all of its preferred embodiments that the agitator comprises a motor, a drive shaft, and at least one propeller located close to the water surface at a depth where the hydrostatic pressure of water is nonexistent or almost nonexistent. This results in energy efficient agitation.

It is preferable in the system of the invention that the drive shaft of said at least one propeller be provided above the water surface with a guard for spreading the water ejected upward by said at least one propeller over an extensive area in the air space as the water strikes against the guard. This further enhances absorption of carbon dioxide into water in the absorption tank or desorption from water in the desorption tank.

In the system of the invention, the agitator has its motor in a particularly preferred case provided with a protective housing, which includes an upside down U-pipe having its one end opening inside the protective housing and its other end outside the housing into the air space of the absorption and/or desorption tank. Thereby is generated the same pressure inside and outside the motor, thus preventing gas from leaking through the motor's drive shaft bearing, which would result in the bearing lubrication being washed away— and dissolved partly because of a gas flow, but also because of the solvent property of carbon dioxide. In addition, e.g. flue gases may contain ash or the like, which in turn soils the discussed bearing. If there is an equal pressure on both sides of the bearing, the soiling problem shall not arise.

In the system of the invention, the agitator has its shaft and at least one propeller preferably surrounded by guide pipe which conducts the water upwards above the water surface. This way is ensured that the propeller is not forced to reverse the direction of water moving in an opposite direction, which would consume more energy.

In a particularly preferred embodiment for the system of the invention, between the pressurizing means and the absorption tank is located a pre-reactor, which is supplied with the pressurized gas and with the water returning from the desorption tank back into the absorption tank and in which the pressurized gas and the water returning from the desorption tank become mixed due to a mixing effect resulting from a difference between the relative flow rates thereof. The benefit gained this way is that pre-agitation need not be supplied with energy from outside and that use is made of intrinsic energy created by the system.

In another preferred embodiment for the system of the invention, the recovering means for the carbon dioxide desorbed from the water in the desorption tank are followed by a feedback for recycling at least a part of the desorbed carbon dioxide back into the absorption tank via the pre-reactor. Thereby pure carbon dioxide is introduced into the flue gas, whereby the partial pressure of carbon dioxide increases and absorption improves in the same ratio, according to Henry's law.

It is also preferable that the system of the invention be provided downstream of the gas pressurizing means with a first heat pump by means of whose condenser the pressurized gas is capable of being heated prior to being mixed with the water. In addition to this, it is preferable that the water departing from the desorption tank be cooled by an evaporator of the first heat pump prior to being conducted back into the absorption tank. The hotter the gas and/or the colder the water, the more efficient is the absorption of carbon dioxide into the water.

In another preferred embodiment for the system of the invention, the absorption tank is followed by a second heat pump by means of whose condenser the water departing from the absorption tank is capable of being heated prior to being conducted into the desorption tank. In relation to this, it is particularly preferable that the water departing from the desorption tank be cooled by an evaporator of the second heat pump prior to being conducted back into the absorption tank via the pre-reactor. The warmer the water in the desorption tank, the more efficient is the desorption of carbon dioxide from the water.

In yet another preferred embodiment for the system of the invention, the system comprises a third heat pump whose evaporator is located between the evaporator of the second heat pump and the evaporator of the first heat pump, and whose condenser enables friction or excess heat brought to the system by some other process device to be eliminated from the system and to be removed to its surroundings or to other utilisation.

It is further preferable for the system according to the invention to comprise a fourth heat pump whose condenser, in a circulation direction of the water, is located between the condenser of the second heat pump and the desorption tank, and via whose evaporator the gas, from which the carbon dioxide has been absorbed in the absorption tank into the water, passes prior to departing from the system. This enables heat of the discussed gas to be recovered for heating the water which has absorbed carbon dioxide and is on its way to the desorption tank.

In a particularly preferred embodiment for the system of the invention, the system further comprises means for producing methanol from carbon dioxide present in the system in the absorption tank or in the desorption tank or at some point of the water circulation, most preferably immediately before the desorption tank. The means for producing methanol consist preferably of an electrolysis reactor by means of which, by breaking up water of the system, is obtained hydrogen which, together with carbon dioxide present in the system, produces methanol. Hence, it is preferred for the system to comprise a distillation unit for recovering the resulting methanol from the water circulation.

The method according to the invention is characterized by agitating water in the absorption tank with an agitator which enables the water to circulate in the absorption tank by ejecting it into an air space of the absorption tank and by spreading it in the absorption tank's air space over an area as extensive as possible. What is achieved this way is that the carbon dioxide contained in a gas, such as e.g. in a flue gas, will be absorbed as effectively as possible into a mass of water contained in the absorption tank.

One preferred embodiment for the method of the invention comprises agitating water in the desorption tank with an agitator which enables the water to circulate in the desorption tank by ejecting it into an air space of the desorption tank and by spreading it the desorption tank's air space over an area as extensive as possible. What is achieved this way is that the carbon dioxide of water that has been conducted from the absorption tank into the desorption tank and that has absorbed carbon dioxide therein will be desorbed as effectively as possible in the desorption tank.

In the method of the invention, it is particularly preferable that water be agitated with an agitator, comprising a motor, a drive shaft, and at least one propeller which is located close to the water surface at a depth where the hydrostatic pressure of water is nonexistent or nearly nonexistent. The motor is preferably an electric motor.

It is further preferable in the method of the invention that the pressurized gas and the water returning from the desorption tank back into the absorption tank be supplied into a pre-reactor in which the pressurized gas and the water returning from the desorption tank are mixed due to a mixing effect resulting from a difference between the relative flow rates thereof, after which the premixed pressurized gas and the water are conducted into the absorption tank. The benefit gained this way is that pre-agitation need not be supplied with energy from outside and that use is made of intrinsic energy created by the system.

In the system and method of the invention, the adjustment of temperature will be more economical as it is no longer necessary to cool or heat a mass of water as large as in prior art solutions. In absorption, cooling of water is preferable from the standpoint of efficiency and so is heating in desorption. In absorption, $CO_2$ condenses in amongst water molecules, thus generating heat according to the laws of physics (PV/T=constant). In desorption, respectively, the gas discharges away and expands, thus cooling by nature. Another influencing factor is naturally a change of pressure.

One preferred embodiment is to supplement the system and method of the invention with the production of methanol. In the process of using electrolysis to produce hydrogen by breaking up water, the hydrogen produced in electrolysis reacts eagerly with carbon dioxide dissolved in water in the system and method of the invention. The oxygen created at the same time is conducted to utilisation or, along with outlet gases, into the environment. The electrolysis reactor can be housed in the absorption or desorption tank or present as a separate reactor at some point of the water circulation, preferably immediately downstream of the desorption tank. In addition, the system and method of the invention involve in this case the use of a distillation unit, which removes methanol from the water circulation to utilisation. Its preferred location is either upstream or downstream of the desorption tank.

When there is methanol in the water circulation, the resulting benefits are as follows: The absorption of carbon dioxide is enhanced to more than tenfold and enables the use of temperatures lower than 0° C. preferable for the absorption of carbon dioxide. The adjustability of a method according to the invention is improved as absorption powers can be adjusted with the amount of methanol. The method, which is a sort of process, works also at temperatures below the freezing point as the hazard of freezing can be avoided. The acquisition costs of the method or process become lower, because the enhancing absorption of carbon dioxide reduces the amount of water volume and the size of tanks, as well as pumping capacities in water circulation. Likewise, the system pressure can be reduced, in which case the compressor is more affordable. Methanol is very suitable with heat pumps as the latter are capable of providing major temperature changes, whereby the extensive temperature range afforded by methanol is put to full use. The continuous production of methanol eliminates the regeneration of methanol required in methanol processes. The distillation of methanol yields a pure end product.

Even when ending up in nature, methanol does not cause permanent changes as it evaporates quickly and has long experience e.g. as a car windshield washer fluid. Methanol is also a useful chemical employed by industry and has worldwide markets. Methanol is a good medium for energy storage, it is a liquid in the condition of normal temperature and pressure, i.e. in NTP condition, and its energy density per unit volume is quite high, e.g. about 450-fold with respect to natural gas (methane) in NTP condition.

When produced by electrolysis, hydrogen appears also in the form of individual atoms, which is a labile condition. It is highly susceptible to merge either with another hydrogen atom or with a carbon dioxide molecule, thereby favorably producing methanol according to the following formula:

$CO_2 + 3H_2 = CH_3OH + H_2O - 11,9$ kcal/mol. Here, the hydrogen is present in the form of molecules as in the formula, or in the form of individual atoms or a combination thereof, but the process is exothermal. Catalysts are needed here, and several of those are available on the market.

In a methanol-producing system for the recovery of $CO_2$, it is possible to control heat pumps, the flow of water, the amount of methanol in circulation, as well as the proportion of resulting $CO_2$ and methanol, in each situation in an economically optimized manner. Should e.g. excess electricity be on offer, the methanol production can be increased as long as the absorption of $CO_2$ is enhanced at the same time e.g. by cooling the water arriving in the absorption tank. In the reverse case, the production of $CO_2$ is maximized. Thus, the process adapts to desired conditions once the control system is modeled with all options.

BRIEF DESCRIPTION OF DRAWINGS

The invention will now be described in detail by way of example with reference to the accompanying drawings, in which.

DETAILED DESCRIPTION

Figure 1:
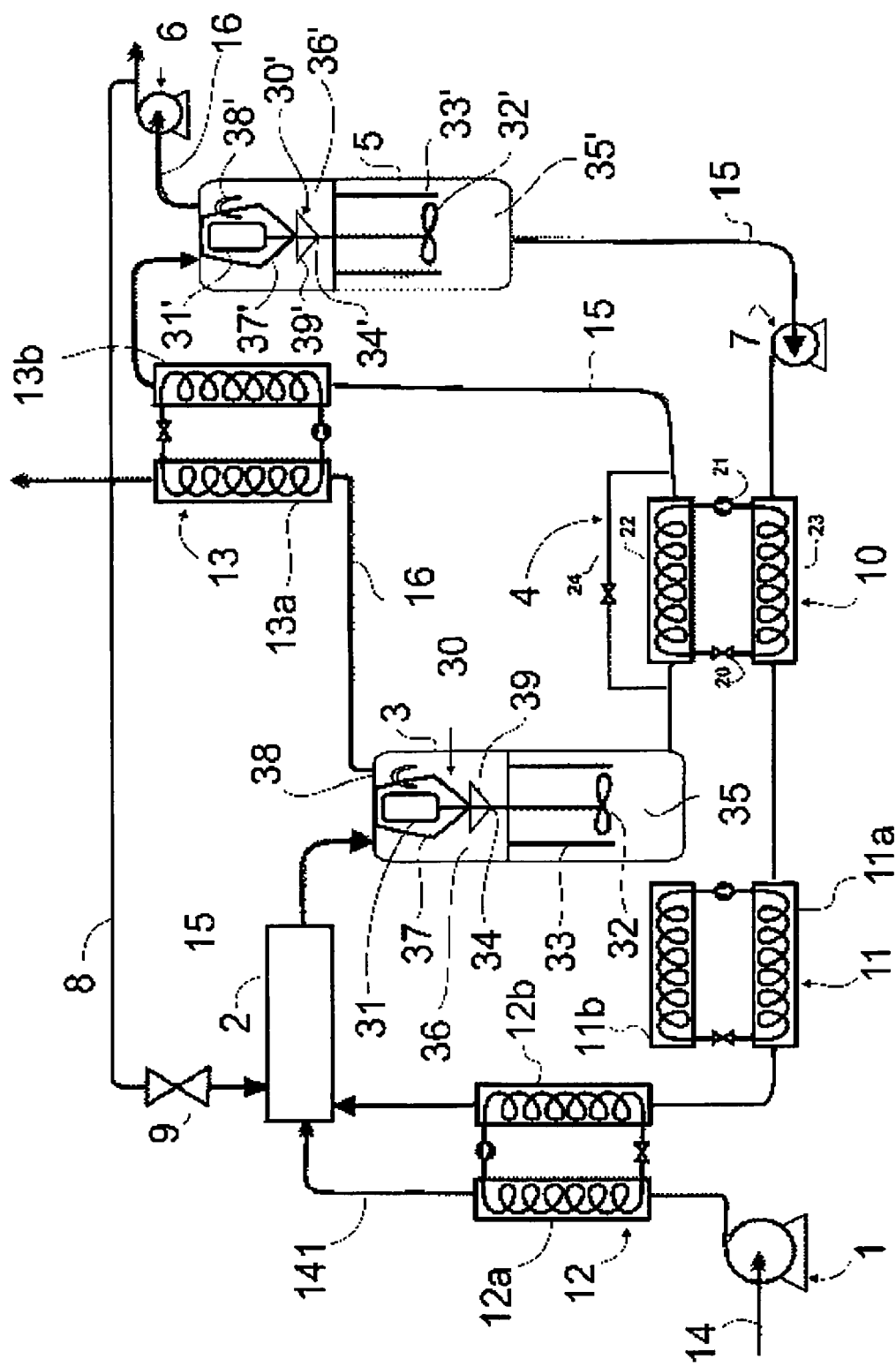
FIG. 1 is a process diagram for a first embodiment of the system according to the invention.

The system illustrated in FIG. 1 for the recovery of carbon dioxide from a gas 14 containing it is particularly suitable for the recovery of carbon dioxide from flue gases. The recovery of carbon dioxide from gas proceeds by first absorbing carbon dioxide into water in an absorption tank 3 and by removing other gases from the system, and then by desorbing carbon dioxide from water in a desorption tank 5, thereby obtaining pure carbon dioxide in gaseous form.

The carbon dioxide-containing gas 14 is first pressurized with pressurizing means 1 shown in FIG. 1, which in this example consist of a compressor, into the form of a pressurized gas 141 which is conducted into a pre-reactor 2 for being premixed with water 15 to be supplied into the pre-reactor. Downstream of the gas pressurizing means 1 follows a first heat pump 12 whose condenser 12a is used for heating the pressurized gas 141 prior to being mixed with water 15, 35. On the other hand, the first heat pump 12 uses its evaporator 12b for cooling the water 15 to be conducted from the desorption tank 5 into the pre-reactor 2. From the pre-reactor 2, the premixed pressurized gas 141 and water 15 are then delivered into the absorption tank 3. Premixing enhances the process and makes use of a flow difference between gas and water without using other energy. Premixing may also be of an injector type.

The absorption tank 3 houses an agitator 32 with a function of enabling water to circulate in the absorption tank 3 by ejecting it into an air space 36 of the absorption tank and by spreading it in the air space of the absorption tank 3 over an area as extensive as possible. The desorption tank 5 has also a similar agitator 32' with a function of enabling water to circulate in the desorption tank 5 by ejecting it into an air space 36' of the desorption tank and by spreading it in the air space of the desorption tank 5 over an area as extensive as possible.

The absorption tank's agitator 30 comprises an electric motor 31, a drive shaft 34, and a propeller 32 which is located close to the water surface at a depth where the hydrostatic pressure of water is nonexistent or nearly nonexistent. The desorption tank 5 comprises respectively a similar electric motor 31', a drive shaft 34', and a propeller 32' which is located close to the water surface at a depth where the hydrostatic pressure of water is nonexistent or nearly nonexistent. Each agitator 30 and 30' has the drive shaft 34, 34' of its propeller 32, 32' provided with a guard 39, 39' for spreading the water ejected upward by said propeller over an extensive area in the air space 36, 36' as the water strikes against the guard 39, 39'. Each guard 39 and 39' is in this example a downward tapering plate. The guard can also be designed in some other shape.

Each agitator 30 and 30' has its motor 31, 31' provided with a protective housing 37, 37', including an upside down U-pipe 38, 38' one end of which opens inside the protective housing 37, 37' and the other end of which opens outside the housing into the air space 36 of the absorption tank 3 and into the air space 36' of the desorption tank 5. What is achieved by means of the U-pipe 38, 38' is pressure equalization on either side of a bearing (not shown in the figure) of the motor 31, 31' of each agitator 30 and 30'.

Without a protective housing for the agitators, it would be difficult to keep the motor dry, especially in the absorption tank which is pressurized. It is by way of a shaft seal that pressure is leaking. If the motor is outfitted with a separate housing, inside which prevails the same pressure as in the tank, the motor remains dry with liquid or gas no longer moving through the shaft. Thus, even the bearing lubrication is not washed away, which is important as carbon dioxide is a solvent. This pressure for a motor space can be extracted from the entire tank or it can be supplied via a connection of the cover.

Each agitator 30, 30' has its shaft 34, 34' and its propeller 32, 32' surrounded by a guide pipe 33, 33' which conducts and raises the water 35 of the absorption tank 3 into the absorption tank's air space 36 and, respectively, the water 35' of the desorption tank 5 into the air space 36' of the desorption tank 5. From the absorption tank 3, the water 35 with absorbed carbon dioxide is conducted into the desorption tank 5 by means of a pump 7, located downstream of the desorption tank 5 in the system's water circulation 15, first via a condenser 22 of a second heat pump 10 and then via a condenser 13b of a fourth heat pump 13 into the desorption tank 5. This interval must be dimensioned to tolerate partially gasified carbon dioxide. The condensers 22 and 13b are used for heating the water with absorbed carbon dioxide for enhancing desorption of carbon dioxide taking place in the desorption tank.

Carbon dioxide 16 (in gaseous form) desorbed from the water 35' in the desorption tank 5 is recovered with recovering means 6, which consist of a compressor. Downstream of the recovering means 6 is disposed a feedback 6 for recycling at least a part of the desorbed carbon dioxide 16 back into the absorption tank 3 via a pre-reactor 2. By virtue of an increase in the partial pressure, the feedback of separated $CO_2$ to absorption improves the absorption more than the energy required for the same.

The desorption of carbon dioxide is followed by conducting the water present in the desorption tank 5 first via an evaporator of the second heat pump 10, then via an evaporator 11a of a third heat pump 11, and then via an evaporator 12b of the first heat pump 12 back into the pre-reactor 2. The evaporators 23, 11a and 12b are used for cooling the temperature of water 15 passing via the pre-reactor 2 back into the absorption tank 3 to a suitable coldness for the effective absorption of carbon dioxide into water in the absorption tank 3.

It is by means of the condenser 11b of the third heat pump 11 that friction or excess heat brought to the system by some other process device can be eliminated from the system and removed to its surroundings or other utilisation.

In the pre-reactor 2 is developed, from a difference between the flow rates of the pressurized gas 141 to be conducted there and the water 15, a considerable mixing effect because the gas 141 (flue gas) has a flow rate which is about 10-fold with respect to the water. It can be optionally further provided with various blenders.

Should the process be void of heat regulating devices, the water would thus be heated in the absorption tank 3 and cooled to the same extent in the desorption tank 5. In addition, water tends to become heated by frictions of the devices.

Figure 2:
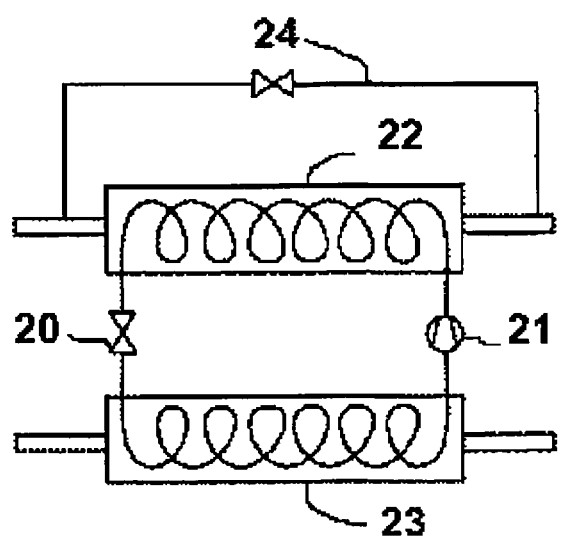
FIG. 2 is merely an enlargement of a heat pump 10 appearing in FIG. 1.

In the system of FIG. 1, all heat pumps 10, 11, 12 and 13 are compressor-based, i.e. are provided not only with a condenser and an evaporator but also with a compressor and a throttle valve. This is illustrated by way of example more precisely in FIG. 2 with regard to the heat pump 10. The second heat pump 10 includes a condenser 22, an evaporator 23, a compressor 21 and a throttle valve 20.

It is from the absorption tank 3 that slightly warmed-up water 15 arrives at the condenser 22 of the second heat pump 10 and from the desorption tank 5 back into the evaporator 23 of the second heat pump 10, cooling in the latter back to a low temperature favorable for absorption. In this case, water is heated by the condenser 22, whereby desorption is improved. In the dimensioning of the second heat pump 10, the ratio between the capacities of the condenser 22 and the evaporator 23 is adapted according to an intrinsic demand of the process while considering also seasonal differences. For example, the saturation point of water for carbon dioxide changes in such a way that, with the pressure of 10 bars at 0° C., it is about 30 g/l and at 20° C. only about 12 g/l. Thus, in absorption, in which it is desirable to have as much $CO_2$ as possible absorbed into water, the objective is to be near 0° C., and in desorption, in which it is desirable for $CO_2$ to remove itself from water, e.g. 20° C. or higher would be good.

What must be further taken into consideration in dimensioning is the ratio between operational efficiency and operating costs. As for control, the most important aspect is the adjustment of absorption temperature to slightly higher than 0° C. The water temperature for desorption adapts then to the aforesaid ratio, but it can be adjusted by means of a bypass valve 24 for the condenser 22 of the second heat pump 10. If the discussed bypass is on the side of the condenser 22, as in FIGS. 1 and 2, the opening thereof turns down the heating of water 15 going to desorption, because a part of the water 15 circumvents the heat exchanger or condenser 22. A bypass pipe, which houses the bypass valve 24, is constructed of a pipe thinner than a main pipe extending through the condenser 22 such that the heat pump 10 could never be completely circumvented and thereby to remove the entire heat pump 10 from its operating range.

The absorption efficiency is influenced not only by water being as cold as possible in the pre-reactor 2 and in the absorption tank 3 but also by having the gas 141 to be supplied therein as hot as possible. This is why the first heat pump 12 is needed. The second heat pump 13 is used to recover and to transfer this heat to desorption. The fourth heat pump 11 relieves the system of friction or excess heat brought therein by some other process device and transfers the same to the environment or other utilisation. In winter, the fourth heat pump 11 is used for adjusting the process conditions to be favorable and for enabling the process to be used outdoors even at sub-zero temperatures. The heat pumps 10, 11, 12 and 13 may be heat exchangers whenever the latter are more favorable in terms of overall economy. The heat pumps enhance the transfer of heat by increasing the temperature differences to become significant in a manner favorable from the standpoint of operation.

The heat pumps increase the temperature gradient and thereby enhance the operation as compared to ordinary heat exchangers. The involved regulating system drops the efficiency of heat transfer if water cools to below a set value, typically to the temperature of 3° C. In the circulating water can also be used methanol or glycol or the like antifreeze. Hence, absorption is improved even further. At the same time, the aforesaid limit changes.

Figure 3:
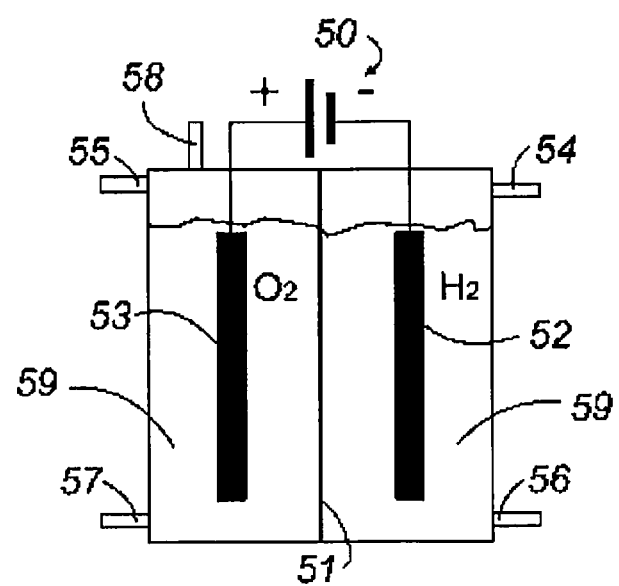
FIG. 3 is a schematic view of an electrolysis apparatus for breaking up water and using the resulting hydrogen at the same time for making methanol in one preferred embodiment of the invention.

By using an electrolysis reactor as shown in FIG. 3, the recovery of carbon dioxide in the above-described system can be enhanced even further. With electrolysis, achieved by means of an electrolysis reactor, the water of the system's water circulation, subsequently referred also as "process fluid", is broken up and from the resulting hydrogen is at the same time produced methanol.

When direct current is fed from a power source (50) of the electrolysis reactor to electrodes 52, 53, at the anode 53 (+) is generated oxygen ($O_2$) which is channeled to utilisation or released to nature via an oxygen outlet 58. At the cathode (52) (−) is generated hydrogen ($H_2$) which reacts with carbon dioxide present in the system, thereby generating methanol ($CH_3OH$).

The electrolysis reactor has an ion permeable membrane 51 which prevents the mixing of gases (oxygen and hydrogen gases). The electrolysis reactor has on the side of its cathode 52, above the surface of a process fluid 59, an inlet 54 for the electrolysis reactor's process fluid, i.e. for the water circulation water 15 used in a system of the invention (cf. FIG. 1), and below the surface of the process fluid 59, an outlet 56 for the process fluid or water circulation 15 back into the water of the water circulation 15. The electrolysis reactor has on the side of its anode 53, above the surface of the process fluid 59, an inlet 55 for a separate water circulation of the system, and below the surface of the process fluid 59, an outlet 57 for the separate water circulation.

The electrolysis reactor can be located anywhere in the process cycle, but it is most preferred to place it wherever water is at its wannest, i.e. downstream of the desorption device 5 shown in FIG. 1 and upstream of the pump 7 of the water circulation 15.

In order to enable the recovery of methanol produced by electrolysis in the system's electrolysis reactor, it is further necessary to include therein a distillation unit (not shown in FIGS. 1-3), which is also advisable to position in connection with the desorption device 5, because when water is heated, it is carbon dioxide which first to separate therefrom. In the distillation unit, temperature is raised to the temperature of 65° C., whereby methanol vaporizes. For methanol production and distillation can only be extracted a side stream from the process water circulation 15 unless the intention is to exploit the production of methanol for something other than the better-than-before control of a carbon dioxide process.

Figure 4:
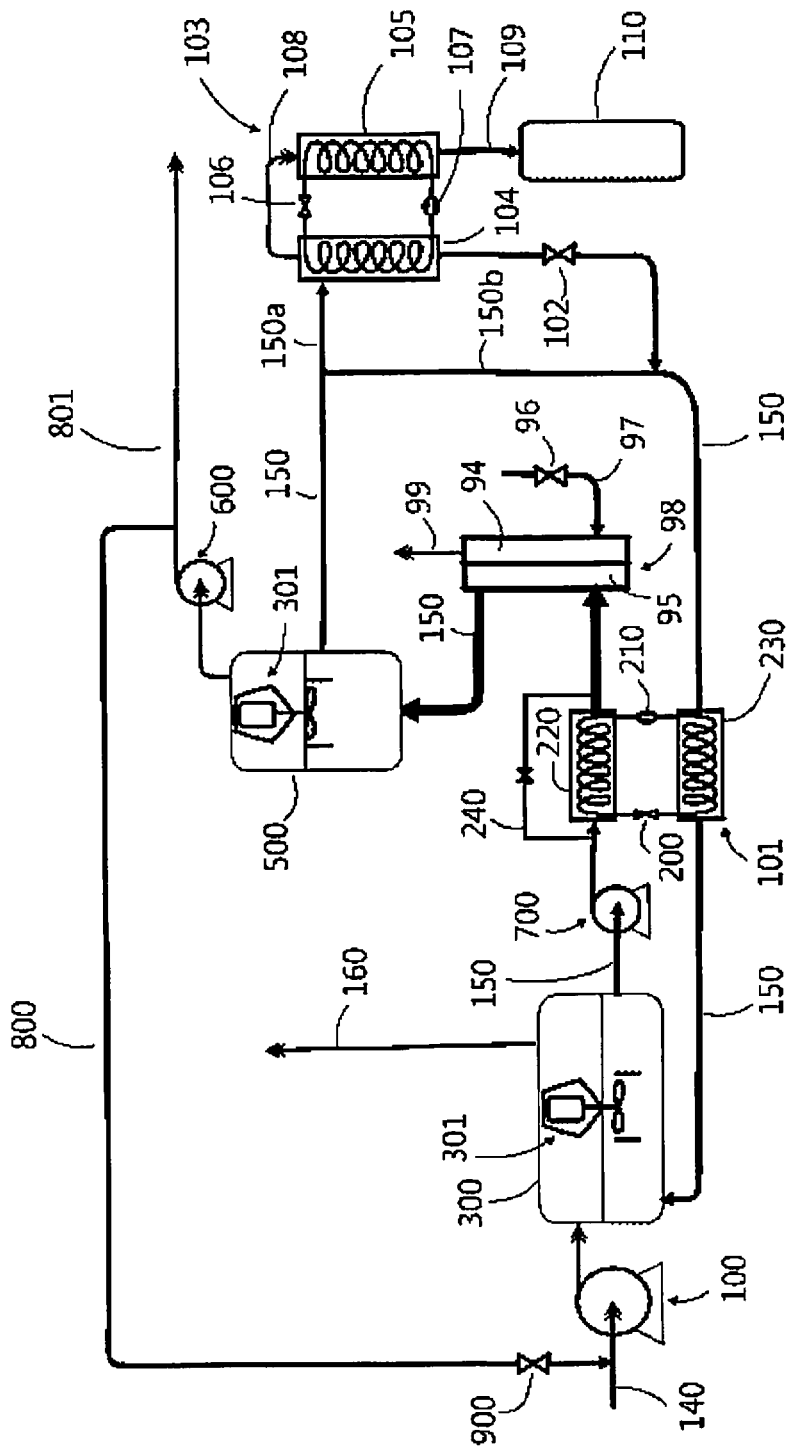
FIG. 4 is a process diagram for a second embodiment of the system according to the invention, which involves the production of methanol from recovered carbon dioxide.

FIG. 4 shows an example of a second embodiment for the system of the invention, which involves the production of methanol from recovered carbon dioxide and in which a distillation unit 103 is also included in the drawing.

The preferred embodiment for the system of the invention, shown in FIG. 4, comprises an absorption tank 300 and an agitator 301 associated therewith, which are similar to those in the system of FIG. 1. The system of FIG. 4 has its desorption tank 500 and an agitator 301 associated therewith matching the desorption tank and its associated agitator of FIG. 1. The most essential differences between the systems of FIG. 4 and FIG. 1 are that, in the system of FIG. 4, the electrolysis reactor is connected to a water circulation 150 upstream of the desorption tank 500, the distillation unit 103 is connected to a portion 150a of the water circulation downstream of the desorption tank 500, and that it is only provided with two heat pumps, a heat pump 101 and a heat pump which functions as the distillation unit 103.

A gas 140 to be cleaned, e.g. a flue gas, which contains carbon dioxide, is pressurized by means of a compressor 100 and conducted into the absorption tank 300, in which the agitator 301 agitates the water therein for enhancing the absorption of carbon dioxide into water. The gas which remains after the absorption of carbon dioxide is channeled out of the system via a conduit 160. From the absorption tank 300, the water is conducted first via a pump 700, then via a condenser 220 of the heat pump 101, and finally via an electrolysis reactor 98 into the desorption tank 500.

In terms of its structure and operation, the heat pump 101 corresponds to the second heat pump 10 shown in FIG. 1, i.e. it includes a condenser 220, an evaporator 230, a compressor 210, and a throttle valve 200. The water 150 departing from the desorption tank 500 circulates via the evaporator 230 of this heat pump 101 back into the desorption tank 300, whereby the water coming from the desorption tank 500 is cooled by the evaporator 230 prior to being conducted back into the absorption tank 300.

The electrolysis reactor 98, which is thus located between the condenser 220 of the heat pump 101 and the desorption tank 500, comprises a cathode-containing cathode side 95 and an anode-containing anode side 94. Via the cathode side 95 the process fluid, i.e. the water in water circulation, proceeds into the desorption tank 500. The anode side 94 and the cathode side 95 are separated from each other by an ion permeable membrane 93, which prevent the mixing of a hydrogen gas being generated on the cathode side and an oxygen gas being generated on the anode side. The ion permeable membrane 93 further prevents the carbon dioxide, and the methanol formed on the cathode side of the electrolysis reactor 98, from migrating into the cathode side 94. The electrolysis reactor 98 further includes an oxygen outlet 99 for recovering or passing out the oxygen gas generated on the cathode side 94.

On the anode side 94, it is advisable to employ salts, e.g. KOH, for improving the conduction of electricity and also required is a makeup or replacement water addition, because otherwise the water broken up into hydrogen gas reduces the amount of water on both electrode sides.

The desorption tank 500 has its air space connected to desorbed carbon dioxide gas recovering means 600, which consist of a compressor, via which the recovered carbon dioxide proceeds. Downstream of the recovering means 600, a part of the carbon dioxide is conducted to a final recovery via a conduit 801, and the rest is conducted via a feedback 800 back into the absorption tank 300 through a compressor 100.

The portion 150a of water departing from the desorption tank 500 is conducted into the distillation unit 103, wherein the methanol present in this water portion 150a is recovered by distilling into a tank 110. The distillation unit 103 has its evaporator 104 vaporizing the methanol, which is present in the water portion 150a and proceeds along a conduit 108 in the form of a methanol vapor into a condenser 105 in which the methanol condenses and is conducted in liquid form into the tank 110. The distillation unit 101 includes a compressor 107 and a throttle valve 106.

From the evaporator 104 of the distillation unit 101, the water of the water portion 150a is conducted via a throttle valve 102 and combined with a second water portion 150b, whereby the water portions 150a and 150b coalesce again to make up the water circulation 150 which is conducted via the evaporator 230 of the heat pump 101 back into the absorption tank 300. Optionally, the absorption tank 300 can have connected thereto a pre-reactor (not shown in FIG. 4) similar to that used in the embodiment of FIG. 1. Hence, the aforesaid re-combined water circulation 150 is conducted via the pre-reactor back into the absorption tank.

By producing methanol from hydrogen gas generated by an electrolysis reactor and from absorbed carbon dioxide present in a water circulation, it is therefore possible to use methanol as an absorbent for carbon dioxide. The excess of produced methanol can be distilled out of the system. Depending on the dimensioning, even all of the carbon dioxide can be turned into methanol. In situations with excess electricity, this is sensible.

The invention claimed is:

1. A method for the recovery of carbon dioxide from a gas which contains it, said method comprising:
   pressurizing the gas;
   absorbing carbon dioxide contained in the pressurized gas into water in an absorption tank;
   desorbing carbon dioxide absorbed in water from water in a desorption tank;
   circulating water from the absorption tank into the desorption tank and from the desorption tank back into the absorption tank; and
   recovering carbon dioxide desorbed from the water,
   wherein water is agitated in the absorption tank with an agitator, comprising a motor, a drive shaft, and at least one propeller which is located close to the water surface at a depth where the hydrostatic pressure of water is nonexistent or almost nonexistent, the agitator enabling the water to circulate in the absorption tank by ejecting it into an air space of the absorption tank and by spreading it in the absorption tank's air space over an area.

2. The method according to claim 1, further comprising agitating water in the desorption tank with another agitator which enables the water to circulate in the desorption tank by ejecting it into an air space of the desorption tank and by spreading it in the desorption tank's air space over an area.

3. The method according to claim 2, wherein the another agitator comprises a motor, a drive shaft, and at least one propeller which is located close to the water surface at a depth where the hydrostatic pressure of water is nonexistent or nearly nonexistent.

4. The method according to claim 1, wherein the pressurized gas and the water returning from the desorption tank back into the absorption tank are supplied into a pre-reactor in which the pressurized gas and the water returning from the desorption tank are mixed due to a mixing effect resulting from a difference between the relative flow rates thereof, after which the premixed pressurized gas and the water are conducted into the absorption tank.

5. The method according to claim 1, including:
   breaking up the water circulation water by means of electrolysis into hydrogen;
   reacting the resulting hydrogen with carbon dioxide in the absorption tank, in the desorption tank or at some point in the water circulation, thereby producing methanol; and
   recovering the resulting methanol optionally and in a desired amount.

6. The method according to claim 1, wherein the agitator further includes a downward tapering guard located above the water surface.

7. The method according to claim 1, wherein the agitator includes:
   a protective housing encapsulating the motor; and
   an upside down U-pipe having one end that opens inside the protective housing and another end that opens outside of the protective housing into the air space of the absorption tank.

* * * * *